United States Patent [19]

Clemence et al.

[11] Patent Number: 4,987,131

[45] Date of Patent: Jan. 22, 1991

[54] 4H-TRIAZOLO[4,3-A][1,4]BENZODIAZE-PINES

[75] Inventors: Francois Clemence; Odile Le Martret, both of Paris; Francois Delevallee, Fontenay sous Bois, all of France

[73] Assignee: Roussel Uclaf, Paris, France

[21] Appl. No.: 491,264

[22] Filed: Mar. 8, 1990

Related U.S. Application Data

[62] Division of Ser. No. 937,709, Dec. 4, 1986, abandoned.

[30] Foreign Application Priority Data

Dec. 13, 1985 [FR] France .............................. 85-18481

[51] Int. Cl.$^5$ .................... C07D 487/04; A61K 31/55
[52] U.S. Cl. ...................................... 514/220; 540/563
[58] Field of Search ......................... 514/220; 540/563

[56] References Cited

U.S. PATENT DOCUMENTS 3,734,922  5/1973  Hester ................................. 540/563
3,880,877  4/1975  Sillstedt et al. ...................... 540/563

Primary Examiner—Glennon H. Hollrah
Assistant Examiner—Patricia L. Morris
Attorney, Agent, or Firm—Bierman and Muserlian

[57] ABSTRACT

Novel 4H-triazolo[4,3-a][1,4]benzodiazepines of the formula

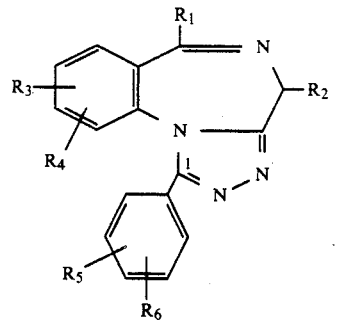

wherein $R_1$ and $R_2$ are individually selected from the group consisting of hydrogen and alkyl of 1 to 5 carbon atoms and $R_3$, $R_4$, $R_5$ and $R_6$ are individually selected from the group consisting of hydrogen, —OH, alkyl and alkoxy of 1 to 4 carbon atoms, —NH$_2$, —NHalk wherein alk is alkyl of 1 to 4 carbon atoms,

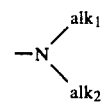

and alk$_1$ and alk$_2$ are individually alkyl of 1 to 4 carbon atoms, halogen, —NO$_2$ and —CF$_3$ in any position of the benzene rings with the proviso that $R_5$ and $R_6$ are not both hydrogen and their non-toxic, pharmaceutically acceptable acid addition salts having good analgesic activity.

6 Claims, No Drawings

4H-TRIAZOLO[4,3-A][1,4]BENZODIAZEPINES

This is a division of Ser. No. 937,209, filed Dec. 4, 1986, now abandoned.

STATE OF THE ART

Pertinent prior art includes U.S. Pat. No. 3,734,922 and European Patent Application Serial No. 0,169,392.

OBJECTS OF THE INVENTION

It is an object of the invention to provide the novel compounds of formula I in racemic or optically active form and their non-toxic, pharmaceutically acceptable acid addition salts and a process for their preparation.

It is another object of the invention to provide novel analgesic compositions and a novel method of combatting pain in warm-blooded animals.

These and other objects and advantages of the invention will become obvious from the following detailed description.

THE INVENTION

The novel compounds of the invention are selected from the group consisting of 4H-triazolo[4,3-a][1,4]benzodiazepines in their racemic or optically active forms of the formula

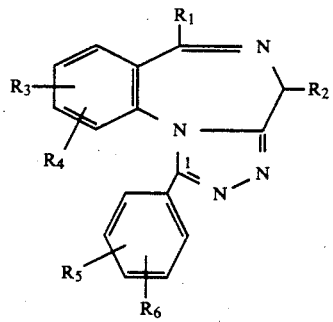

wherein $R_1$ and $R_2$ are individually selected from the group consisting of hydrogen and alkyl of 1 to 5 carbon atoms and $R_3$, $R_4$, $R_5$ and $R_6$ are individually selected from the group consisting of hydrogen, —OH, alkyl and alkoxy of 1 to 4 carbon atoms, —NH$_2$, —NHalk wherein alk is alkyl of 1 to 4 carbon atoms,

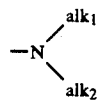

and alk$_1$ and alk$_2$ are individually alkyl of 1 to 4 carbon atoms, halogen, —NO$_2$ and —CF$_3$ in any position of the benzene rings with the proviso that $R_5$ and $R_6$ are not both hydrogen and their non-toxic, pharmaceutically acceptable acid addition salts.

Examples of $R_1$ to $R_6$ as alkyl are methyl, ethyl, n-propyl, isopropyl and n-butyl and suitable halogens are bromine, iodine and preferably chlorine, alk, alk$_1$, and alk$_2$ are preferably methyl, ethyl, isopropyl, n-propyl and n-butyl.

Examples of suitable acids for the preparation of the nontoxic, pharmaceutically acceptable acid addition salts are mineral acids such as hydrochloric acid, hydrobromic acid, sulfuric acid and Phosphoric acid and organic acids such as formic acid, acetic acid, propionic acid, oxalic acid, maleic acid, succinic acid and trifluoroacetic acid.

Among the preferred compounds of formula I are those wherein $R_1$ and $R_2$ are methyl, those wherein $R_3$ and $R_4$ are hydrogen, those wherein $R_5$ and $R_6$ are both methoxy or —CF$_3$ or halogen, those wherein $R_5$ is hydrogen and $R_6$ is halogen, methoxy or —CF$_3$ in racemic or optically active form and their non-toxic, pharmaceutically acceptable acid addition salts.

Specific preferred compounds of the invention are 4,6-dimethyl-1-(4-methoxy-phenyl)-4H-1,2,4-triazolo[4,3-a][1,4]benzodiazepine and 4,6-dimethyl-1-(4-chlorophenyl)-4H-1,2,4-triazolo[4,3-a][1,4] benzodiazepine in their racemic and optically active forms and their non-toxic, pharmaceutically acceptable acid addition salts.

The novel process of the invention for the preparation of the compounds of formula I in their racemic or optically active forms and their acid addition salts comprises reacting a compound of the formula

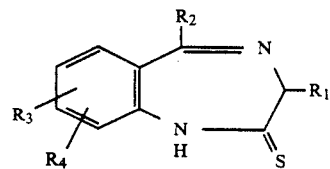

wherein $R_1$, $R_2$, $R_3$ and $R_4$ have the above definitions in their racemic or optically active forms with a compound of the formula

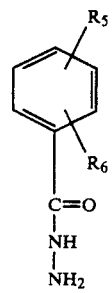

wherein $R_5$ and $R_6$ have the above definitions to obtain a compound of formula I and optionally reacting the latter with an acid to obtain the corresponding acid addition salt. Preferably, the reaction is effected at reflux in an organic solvent such as toluene, tetrahydrofuran, methylene chloride and alcohols.

The novel analgesic compositions of the invention are comprised of an analgesically effective amount of at least one compound of formula I in their racemic or optically active forms and their non-toxic, pharmaceutically acceptable acid addition salts and an inert pharmaceutical carrier or excipient. The compositions may be in the form of capsules, tablets, dragees, granules, suppositories, ointment, creams, gels, aerosols and injectable solutions or suspensions.

Examples of suitable excipients are talc, arabic gum, lactose, starch, magnesium stearate, cocoa butter, aqueous or nonaqueous vehicles, fatty substances of animal or vegetable origin, paraffin derivatives, glycols, various wetting, dispersing and emulsifying agents or preservatives.

The compositions of the invention are useful for the treatment of various pains of muscular, articular or nervous origin, toothaches, migraines, shingles as well as a complementary treatment in the treatment of infectious and feverish conditions. They are also useful for the treatment of degenerative inflammatory illnesses such as osteoarthrosis, various collagenoses (tendinites, etc.), rheumatic illnesses, (rheumatoid polyarthritis, ankylosing spondylarthritis), as well as in the treatment of other illnesses of autoimmune nature such as disseminated lupus erythematosus, glomerulonephritis, and multiple sclerosis.

The novel method of the invention for relieving pain in warm-blooded animals, including humans, comprises administering to warm-blooded animals an analgesically effective amount of at least one compound of formula I and its non-toxic, pharmaceutically acceptable acid addition salts. The compounds may be administered orally, rectally, parenterally or topically to the skin and mucosa. The usual daily dose depends on the condition treated, the method of administration and the specific compound. The usual oral dose is 0.25 to 25 mg/kg per day.

The starting compounds of formula II may be prepared as in U.S. Pat. No. 3,734,922 by heating a compound of the formula

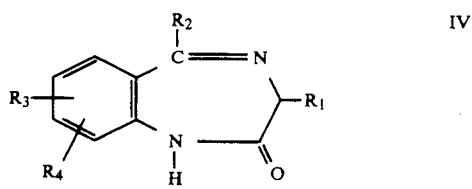

wherein $R_1$ to $R_4$ the above definitions with phosphorus pentasulfide.

In the following examples there are described several preferred embodiments to illustrate the invention. However, it should be understood that the invention is not intended to be limited to the specific embodiments.

EXAMPLE 1

4,6-dimethyl-1-(4-methoxyphenyl)-4H-1,2,4-triazolo[4,3-a][1,4]benzodiazepine

STEP A: 1,3-dihydro-2-thioxo-3,5-dimethyl-2H-1,4-benzodiazepine 10.2 g of phosphorus pentasulfide were introduced into a mixture of 13.33 g of 1,2-dihydro-3,5-dimethyl-2H-1,4-benzodiazepine-2-one (prepared according to French Patent No. 1,326,838), 160 ml of chloroform, 13.3 ml of hexamethyl phosphotriamide and the mixture was refluxed for 4 hours. The chloroform was expelled under reduced pressure and 200 ml of a saturated solution of sodium bicarbonate were slowly added to the residue to adjust the pH to 9-10. The mixture was diluted with 50 ml of water and was stirred at room temperature under reduced pressure until the gum thickened. After separating, rinsing, and drying under reduced pressure, the residue was triturated at reflux in 300 ml of ethyl acetate. Activated charcoal was added and the mixture was refluxed for 5 minutes, filtered hot and the insoluble material was rinsed hot. The filtrate was concentrated to dryness under reduced pressure and the solvents of the crystallized product were eliminated by entrainment under reduced pressure with 20 ml of isopropyl ether. The residue was taken up in 40 ml of isopropyl ether, triturated, separated, rinsed with isopropyl ether and dried under reduced pressure to obtain 7.75 g of 1,3-dihydro-2-thioxo-3,5-dimethyl-2H-1,4-benzodiazepine with a specific rotation of $[\alpha]_D = -80° \pm 2.5°$ (c=0.5% CHCl$_3$).

STEP B: 4,6-dimethyl-1-(4-methoxyphenyl)-4H-1,2,4-triazolo[4,3-a][1,4% benzodiazepine A mixture of 8.43 g of 1,3-dihydro-2-thioxo-3,5-dimethyl-2H-1,4-benzodiazepine (3S) and 7.5 g of p-methoxy benzoic acid hydrazide in 150 ml of toluene was refluxed for 15 hours and was cooled to 20° C. and dried. The solvents were expelled under reduced pressure to obtain 18.01 g of brown oil which was chromatographed over silica (eluant: methylene chloride-methanol 95-5). The fractions were evaporated to dryness to obtain 8.12 g of gum which was dissolved in ethyl ether and was triturated at reflux to solidify the gum. This separated at 20° C. and was rinsed with ether, triturated in ether to obtain 6.53 g of 4,6-dimethyl-1-(4-methoxyphenyl)-4H-1,2,4-triazolo[4,3-a][1,4]benzodiazepine which was purified by preparation and crystallization of an oxalate.

6.21 of the said product and 2.93 g of oxalic acid were dissolved at reflux and with stirring in 140 ml of isopropanol and the mixture was filtered hot. The filtrate was concentrated under reduced pressure to 100 ml and left to cool to 20° C. The salt obtained was separated, rinsed with an isopropanol-ether mixture and dried under reduced pressure to obtain 4.24 g of product which was taken up in water. Methylene chloride was added to the suspension obtained and the mixture was made alkaline by addition in fractions of sodium bicarbonate and was decanted and extracted with methylene chloride. The combined organic phases were washed with water until neutral, dried, treated with activated charcoal and evaporated to dryness under reduced pressure. The resin obtained was taken up in hot ether and after cooling, the crystals obtained were separated, dried under reduced pressure at 20° C., then at 60° C. to obtain 3.26 g of expected product melting at 195° C.

EXAMPLE 2

4,6-dimethyl-1-(4-chlorophenyl)-4H-1,2,4-triazolo[4,3-a]1[1,4]benzodiazepine

Using the procedure of Example 1, 25 g of the compound of formula II, 450 ml of toluene and 23 g of 4-chlorobenzoic acid hydrazide were refluxed for 24 hours and then the solvent was evaporated under reduced pressure. The residue was taken up with ethyl acetate, dried and treated with activated charcoal, then concentrated to dryness. The 50 g of crude product obtained were dissolved in 150 ml of tetrahydrofuran and a solution of 15.6 g of oxalic acid in 120 ml of tetrahydrofuran was added with stirring. The crystals were separated, washed with tetrahydrofuran, then with ethyl ether and dried to obtain 8.4 g of product melting at 220° C. The product was taken up in 50 ml of water and 6 g of sodium bicarbonate were added slowly. The mixture was extracted with methylene chloride and the extracts were washed with water, dried and concentrated to dryness to obtain 5.6 g of 4,6-dimethyl-1-(4-chlorophenyl)-4H-1,2,4-triazolo[4,3-a][1,4]benzodiazepine melting at 230° C.

Analysis: $C_{19}H_{15}N_4Cl$; molecular weight=382.801: Calculated: % C 66.98; % H 4.68; % N 17.36; % Cl 10.98; Found: 67.1; 4.80 17.2; 10.8.

The following compounds could be prepared in an analogous fashion.

4,6-dimethyl-1-(3,4-dimethoxyphenyl)-4H-1,2,4-triazolo[4,3-a][1,4]benzodiazepine;

4,6-dimethyl-1-(2- or 3-chlorophenyl)-4H-1,2,4-triazolo[4,3-a][1,4]benzodiazepine;

4,6-dimethyl-1-(2-, 3- or 4-bromophenyl)-4H-1,2,4-triazolo[4,3-a][1,4]benzodiazepine;

4,6-dimethyl-1-(2-, 3- or 4-fluorophenyl)-4H-1,2,4-triazolo[4,3-a][1,4]benzodiazepine;

4,6-dimethyl-(2,4- or 2,5-dichlorophenyl)-4H-1,2,4-triazolo[4,3-a][1,4]benzodiazepine;

4,6-dimethyl-1-(2,4- or 2,5-dibromophenyl)-4H-1,2,4-triazolo[4,3-a][1,4]benzodiazepine;

4,6-dimethyl-1-(2,4- or 2,5-difluorophenyl)-4H-1,2,4-triazolo[4,3-a]1,4]benzodiazepine;

4,6-dimethyl-1-(3- or 4-trifluoromethylphenyl)-4H-1,2,4-triazolo[4,3-a][1,4]benzodiazepine; as well as their salts of addition with acids.

EXAMPLE 3

Tablets were prepared containing 50mg of the product of Example 1 and sufficient excipient for a tablet weighing 350 mg of lactose, talc, starch and magnesium stearate.

PHARMACOLOGICAL STUDY

A. Action on biosynthesis of prostaglandins in vitro.

Arachidonic acid is converted into prostaglandins (PGs) of series 2 by a cyclo-oxygenase contained in a microsomal preparation of seminal vesicles of a bull carried out according to the Tagekuchi et al method [Mechanism of prostaglandin biosynthesis. I characterization and essay of bovine prostaglandin synthetase. Biochemistry, 1971, 10, 2372]. The precursor, at contraception of $15 \times 10^{-6}$M, was incubated for 30 minutes at 37° C. in the presence of a fixed concentration in proteins of the preparation of seminal vesicles and of the product of Example 1. After blocking the reaction by immersion in boiling water for one minute, then centrifuging, the prostaglandins were evaluated by radioimmuno test inspired by that of Dray et al [Radioimmunoessay of prostaglandins F, $E_1$ and $E_2$ in human plasma. European J. Clin. Invest., 1975 5, 311]. This enabled the $PGE_2$ and $PGF_2$ alpha to be evaluated specifically and the inhibiting activity of the product ($CI_{50}$) is calculated on the sum of these two prostaglandins. The $CI_{50}$ found was $2 \times 10^{-6}$M.

B. Study of analgesic activity

The test used was stretchings induced by acetic acid described by R. Koster et al [Fed. Proc. 1959, 1B 412] according to which the intraperitoneal injection of acetic acid induces in mice repeated stretchings and torsional movements which can persist for more than 6 hours. Analgesics prevent or decrease this syndrome which can considered as the externalization of a diffuse abdominal pain. The acetic acid was administered at a dose of 100 mg/kg or 1 ml of a 1% aqueous solution per 100 g of body weight and the compound of Example 1 was orally administered half an hour before the injection of acetic acid, the mice having been without food for 7 hours. The stretchings were observed and counted for each mouse for a period of observation of 15 minutes and the results were expressed as active dose 50 which is the dose which enabled a decrease of 50% to be obtained in the number of stretchings in comparison with the control animals. The $DA_{50}$ found was 4 mg/kg.

C. Anti-inflammatory activity was determined by the test for arthritis induced by carrageenin in rats and 0.5 ml of a sterile suspension at 1% of carrageenin was administered in the tibio-tarsal articulation of a back paw in male rats weighing from 130 to 150 g. Simultaneously, the product of Example 1 was orally administered in a suspension of carboxymethylcellulose at 0.25% and of Tween at 0.02%. The volume of the paw was measured before the administration, then 2 hours, 4 hours, 6 hours, 8 hours and 24 hours afterwards. The intensity of the inflammation was at its highest 4 to 6 hours after the injection of carrageenin and the difference in volume of the paws of the treated animals and the control animals was evidence of the anti-inflammatory action of the medicament. The $DA_{50}$ was determined, which was the dose which enabled a decrease in the oedema of 50% to be obtained. For the product of Example 1, the $DA_{50}$ was found to be 50 mg/kg.

Various modifications of the compounds and method of the invention may be made without departing from the spirit or scope thereof and it should be understood that the invention is intended to be limited only as defined in the appended claims.

What we claim is:

1. A compound selected from the group consisting of 4,6-dimethyl-1-(4-methoxyphenyl)-4H-1,2,4-triazolo[4,3-a]benzodiazepine and its non-toxic, pharmaceutically acceptable acid addition salts.

2. A compound selected from the group consisting of 4,6-dimethyl-1-(4-chlorophenyl-4H-1,2,4-triazolo [4,3-a][1,4]benzodiazepine in racemic or optically active form and its non-toxic, pharmaceutically acceptable acid addition salts.

3. An analgesic composition comprising an analgesically effective amount of the compound of claim 1 and an inert carrier.

4. An analgesic composition comprising an analgesically effective amount of the compound of claim 2 and an inert carrier.

5. A method of relieving pain in warm-blooded animals comprising administering to warm-blooded animals an analgesically effective amount of the compound of claim 1.

6. A method of relieving pain in warm-blooded animals comprising administering to warm-blooded animals an analgesically effective amount of the compound of claim 2.

* * * * *